United States Patent
Wagner

(10) Patent No.: US 8,784,106 B1
(45) Date of Patent: Jul. 22, 2014

(54) DENTAL PREPARATION DELIVERY SYSTEM

(71) Applicant: Eugene C. Wagner, Pacific Palisades, CA (US)

(72) Inventor: Eugene C. Wagner, Pacific Palisades, CA (US)

( * ) Notice: Subject to any disclaimer, the term of this patent is extended or adjusted under 35 U.S.C. 154(b) by 0 days.

(21) Appl. No.: 13/975,562

(22) Filed: Aug. 26, 2013

Related U.S. Application Data

(60) Provisional application No. 61/855,622, filed on May 20, 2013, provisional application No. 61/855,908, filed on May 28, 2013.

(51) Int. Cl.
*A61C 19/06* (2006.01)
*A61C 15/00* (2006.01)

(52) U.S. Cl.
CPC .................................. *A61C 19/066* (2013.01)
USPC .............................. 433/215; 424/443; 433/80

(58) Field of Classification Search
CPC ........................... A61C 19/063; A61C 19/066
USPC ................................... 424/443; 433/215, 80
See application file for complete search history.

(56) References Cited

U.S. PATENT DOCUMENTS

| | | | |
|---|---|---|---|
| 5,165,424 A | 11/1992 | Silverman | |
| 5,611,687 A | 3/1997 | Wagner | |
| 5,891,453 A | 4/1999 | Sagel | |
| 7,114,953 B1 | 10/2006 | Wagner | |
| 2006/0099550 A1* | 5/2006 | Faasse et al. | 433/215 |

OTHER PUBLICATIONS

Henry Schein Dental. Waxes—Boxing Wax. Retrieved on Jan. 15, 2014.*
Henry Schein Dental. Waxes—Base Plate Wax. Retrieved on Jan. 15, 2014.*
TheFreeDictionary.com. Base Plate Wax. Retrieved on Jan. 15, 2014.*

* cited by examiner

*Primary Examiner* — Frederick Krass
*Assistant Examiner* — Tracy Liu
(74) *Attorney, Agent, or Firm* — Seth Natter; Natter & Natter

(57) ABSTRACT

A dental preparation delivery system includes a soft malleable wax sealing strip bonded to a wax base strip. The peripheral outline of a model dentition extends into the thickness of the sealing strip to form a receptacle. A border of the sealing strip completely surrounds the outline. The receptacle is filled with a dental preparation to be administered and the sealing strip is overlaid with a film. In use, the film is removed, the system is bent to an arch shape and the outline is registered with the user's buccal dentition. Lateral force is applied in a lingual direction against the base strip to reshape the sealing strip for sealing contact of the border against the periphery of the user's buccal dentition, while leaving the preparation in contact with remaining buccal surfaces.

22 Claims, 4 Drawing Sheets

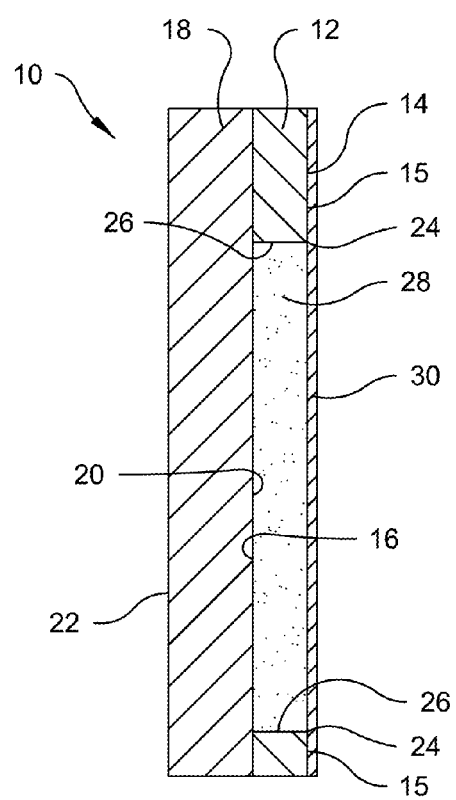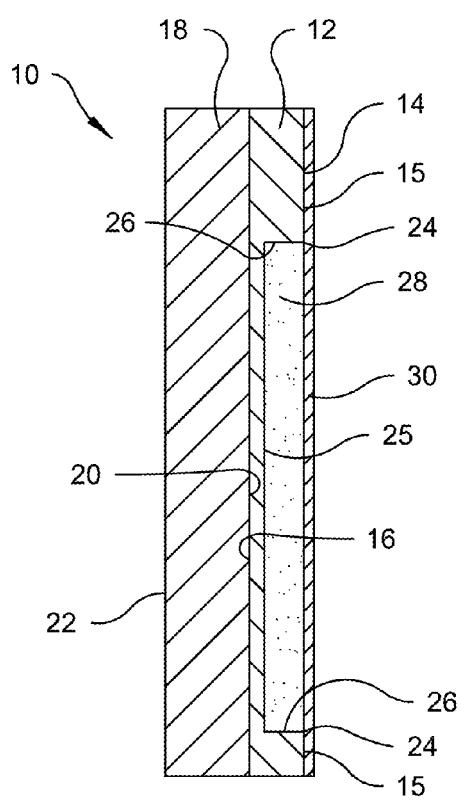
*Fig. 2*  *Fig. 3*

DENTAL PREPARATION DELIVERY SYSTEM

RELATED APPLICATIONS

This application claims the benefit of Provisional Application No. 61/855,622 filed May 20, 2013 and Provisional Application No. 61/855,908, filed May 28, 2013, the entirety of each of which is incorporated herein by reference.

BACKGROUND OF THE INVENTION

1. Field of the Invention

The present invention relates generally to the treatment of conditions in the oral cavity and more specifically to a delivery system for applying a preparation, e.g. bleach, desensitizing agent, anticariogenic agent, antimicrobial agent, fluoride, etc., to the surfaces of teeth.

2. Antecedent Technology

Significant advances in the art of tooth whitening have evolved in recent years. Tooth whitening is no longer relegated to the costly and time consuming procedures rendered by the dental practitioner. Various approaches have evolved for practicing tooth whitening procedures without participation of the dental practitioner.

Among the early tooth whitening systems for do-it-yourself usage was a paste or gel containing a hydrogen peroxide or carbamide peroxide constituent. The gel or paste was applied to tooth surfaces by, for example, a toothbrush, a cotton swab, etc.

Unfortunately, such systems failed to provide readily noticeable results, due to a combination of factors including the limited time duration of application as well as the dilution of effective whitening or bleaching constituent within the oral cavity by saliva. Further, gingival surfaces were engaged by the whitening or bleaching constituent, leading to possible gingival initiation or other undesired effects.

One approach at providing an effective delivery system for a tooth whitening preparation on buccal enamel surfaces of target teeth included the system disclosed in U.S. Pat. No. 5,611,687 which issued Mar. 18, 1997 to applicant herein. Such system comprised and applicator for carrying and applying a liquid preparation solely upon buccal surfaces of target teeth, i.e. teeth which are visible when talking, smiling, etc. The liquid preparation was drawn to an applicator tip by capillary action. To administer a coating of the tooth whitening preparation on selected tooth enamel surfaces, the tip was wiped over the surfaces to be treated. The efficacy of such delivery system was impeded, however because the liquid preparation was susceptible to saliva dilution.

Other attempts for improving the self administration of tooth whitening preparations included heating a dental tray retainer carrying a moldable material in boiling water, taking an impression of the user's dentition, applying a tooth whitening material to the internal surfaces of the impression and then wearing the custom fit retainer, as disclosed in U.S. Pat. No. 5,165,424 issued Nov. 24, 1992. The system disclosed therein did not attain widespread commercial success, perhaps due to the fact that the device involved difficult procedures and was more suited for implementation by a dental professional. Additionally, the custom fit retainer was bulky and cumbersome and impeded speech and appearance could not, therefore, be worn in any environment wherein social encounters might be anticipated.

A further approach comprised the utilization of flexible strips preloaded with a tooth whitening preparation, as disclosed in U.S. Pat. No. 5,891,453 issued Apr. 6, 1999. The flexible strips disclosed therein were unable to attain a true impression of the user's buccal dentition; they could not intimately enter interdental crevices, for example. Further, the user was not able to control the concentration of tooth whitening preparation or limit the application to selected target teeth or tooth surfaces. A further disadvantage was that the tooth whitening preparation was often in contact with gingival surfaces, which led to gingival irritation.

SUMMARY OF THE INVENTION

A dental preparation delivery system includes a planar laminate of a soft malleable wax sealing strip of uniform thickness which is bonded to a face of a wax base strip having a higher elastic modulus than the sealing strip. The peripheral outline of a model buccal dentition is formed by an interior wall which extends completely or partially through the sealing strip, to form an interior space. The internal wall and that portion of the base strip registered with the interior space or a base or floor portion of the sealing strip forms a receptacle. The receptacle is filled with a dental preparation to be administered and the sealing strip is overlaid with a film such that the preparation is encased within a chamber defined by the film, the internal wall and the face of the base strip or the floor portion of the sealing strip.

The preparation is administered by removing the film to expose the dental preparation, bending the delivery system to an arch shape, registering the peripheral outline with the user's buccal dentition and applying lateral force in a lingual direction to reshape the sealing strip for adherence and sealing contact against the periphery of the user's buccal dentition, while leaving the preparation in contact with remaining buccal surfaces.

From the foregoing compendium, it will be appreciated that it is an aspect of the present invention to provide a dental preparation delivery system of the general character described which is not subject to the disadvantages of the antecedents of the invention aforementioned.

It is a feature of the present invention to provide a dental preparation delivery system of the general character described having a simplified procedure for administration of the preparation.

A consideration of the present invention is to provide a dental preparation delivery system of the general character described which precludes undesirable gingival exposure to preparations being administered.

A further aspect of the present invention is to provide a dental preparation delivery system of the general character described which assures against saliva dilution of the preparation being administered.

To provide a dental preparation delivery system of the general character described which does not impede social discourse is a further consideration of the present invention.

Another feature of the present invention is to provide a dental preparation delivery system of the general character described which is low in cost and suitable for manufacture by economical mass production fabrication.

To provide a dental preparation delivery system of the general character described which is equally suitable for employment in the administration of a variety of dental preparations is a further aspect of the present invention.

Another feature of the present invention is to provide a dental preparation delivery system of the general character described which provides efficacious administration of dental preparation to interstitial tooth surfaces.

A still further aspect of the present invention is to provide a dental preparation delivery system of the general character described which is safe and easy to use.

Yet another feature of the present invention is to provide dental preparation delivery system of the general character described which does not require dentition impressions prior to administration.

Other aspects, features and considerations of the present invention in part will be obvious and in part will be pointed out hereinafter.

With these ends in view, the invention finds embodiment in the various combinations of elements, arrangements of parts and series of steps by which the said aspects, features and considerations aforementioned and certain other aspects, features and considerations are attained, all with reference to the following description and drawings and the scope of which will be more particularly pointed out and indicated in the appended claims.

BRIEF DESCRIPTION OF THE DRAWINGS

In the accompanying drawings, in which are shown one of the various exemplary embodiments of the invention, FIG. 2 is an enlarged scale transverse sectional view through the delivery system, the same being taken along the plane 2-2 of FIG. 1 and showing a dental preparation encased within a chamber formed by an internal wall of the sealing strip which defines the peripheral outline, the face of the base strip and a removable film overlay, FIG. 3 is an enlarged scale transverse sectional view through the delivery system, similar to FIG. 2, but showing the dental preparation encased within a chamber formed by the internal wall of the sealing strip, a base or floor portion of the sealing strip and a removable film overlay

DESCRIPTION OF THE PREFERRED EMBODIMENT

Figure 1:
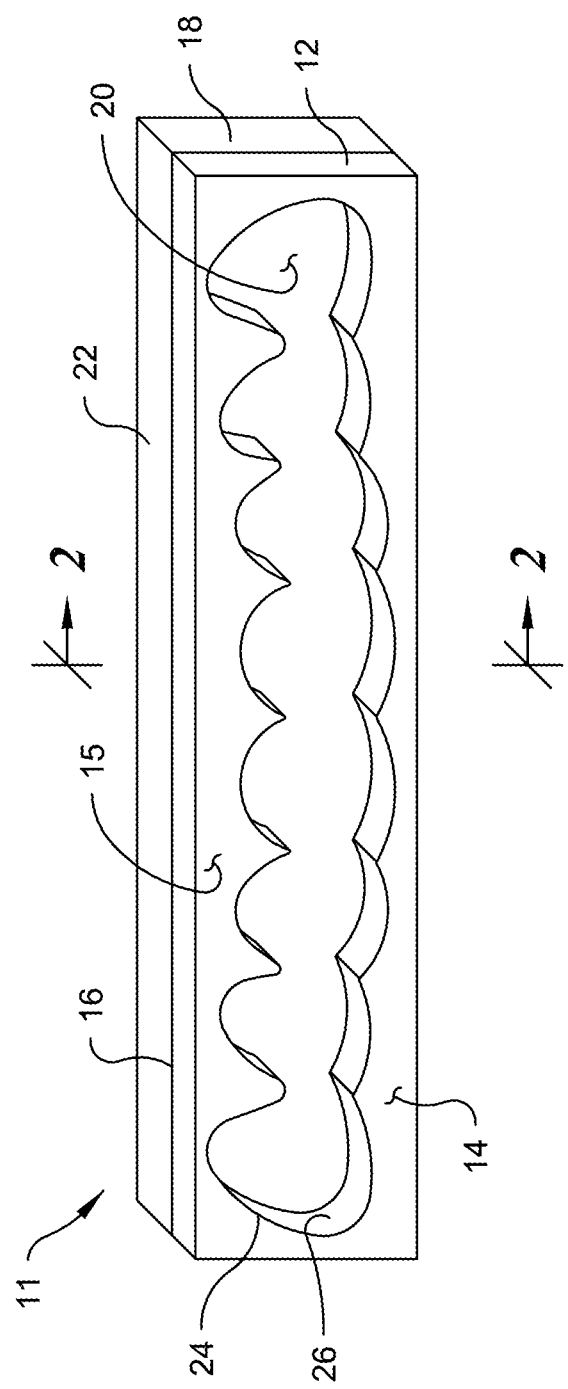
FIG. 1 is a perspective view of a dental preparation delivery system constructed in accordance with and embodying the present invention and showing a sealing strip adhered to the face of a base strip with a cut away interior space bounded by a peripheral outline.

Referring now in detail to the drawings, the reference numeral 10 denoted generally a dental preparation delivery system constructed in accordance with and embodying the invention and adapted for the administration of a dental preparation on buccal tooth surfaces.

The delivery system 10 includes a planar laminate 11 formed of a sealing strip 12 of soft malleable dental grade wax, such as boxing wax, which is paraffin based. The sealing strip 12 includes a pair of generally rectangular parallel proximal and distal faces, 14, 16, spaced apart a distance in the order of 1 mm. to 2 mm., with at least the proximal face 14 being inherently tacky.

Bonded to the sealing strip 12 is a base strip 18 formed of a dental grade wax having a higher elastic modulus than that of the malleable sealing strip 12. Suitable waxes for the base strip 18 include modelling wax and base plate wax. The base strip includes a pair of generally rectangular parallel proximal and distal faces, 20, 22, spaced apart a distance in the order of 2 mm. to 3 mm. In accordance with the invention, the distal face 16 of the sealing strip is bonded to the proximal face 20 of the base strip 18.

A peripheral outline 24 of a model buccal dentition from central incisors to bicuspids, for example, provides an interior space within the sealing strip 12 surrounded by a border 15 which extends from the peripheral outline 24 to the outer edges of the sealing strip 12. The peripheral outline 24 is defined by a continuous internal wall 26 which extends, at its upper limits to the gingival borders of the model dentition and at its lower limits, to the occlusal surfaces thereof.

The internal wall 26 may be die cut completely through the thickness of the strip, molded with the sealing strip 12 or formed by other fabrication methods. For example, a core or die may be forced into the sealing strip 12. If molded, the sealing strip may be compressed or otherwise formed around a core or die which may extend completely through the thickness of the sealing strip or partially through, leaving a thinned flat portion of the sealing strip as a base or floor 25 (illustrated in FIG. 3) surrounded by the internal wall 26. The internal wall 26, together with that portion of the base strip proximal face 20 in registration with the interior space formed by the wall 26, or the thinned floor 25, provides a receptacle for receiving a dental preparation 28, such as a bleaching agent, desensitizing agent, anticariogenic agent, antimicrobial agent, fluoride, etc. After the receptacle is filled with the dental preparation 28, the proximal face 14 of the sealing strip 12 is covered with a thin film overlay 30, illustrated in FIG. 2 and FIG. 3, to seal the dental preparation until it is to be administered.

To administer the dental preparation 28, the user strips the overlay 30 from the proximal face 14 of the sealing strip 12 to expose the dental preparation 28 as well as the tacky surface of the proximal face border 15 surrounding the receptacle. The delivery system is then bent to an arch shape to approximate the curvature of the user's dentition arch and registered with the corresponding surfaces of the user's dentition. The outline 24 can be configured as a maxillary or mandibular dentition and may also be configured of different sized models or of generic geometric shapes which do not conform to specific or model dentitions.

Figure 5:
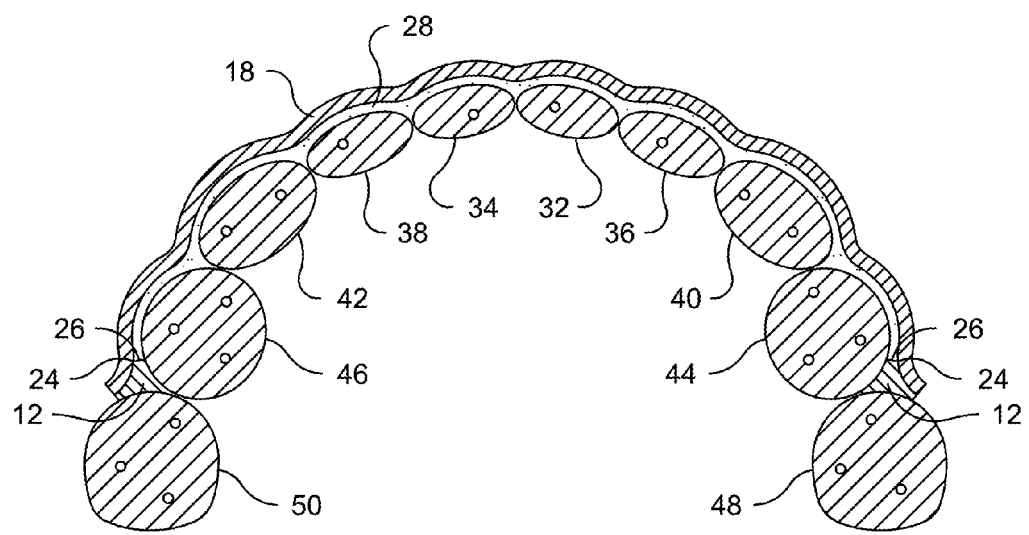
FIG. 5 is a reduced scale sectional view through the dentition and the delivery system during administration of the dental preparation, the same being taken substantially along the line 5-5 of FIG. 4.

Once registered with the user's dentition, lateral pressure is applied in a lingual direction against the distal face 22 of the base strip 18 to deform and shape both the base strip and the sealing strip 12 such that the tacky surface of the sealing strip border 15 conforms to the shape of and adheres to the peripheral outline of the user's buccal dentition including interdental crevices. As illustrated in FIG. 5, wherein the dental preparation 28 is applied to the buccal surfaces of a maxillary dentition arch, the buccal surfaces being simultaneously treated include a pair of central incisors 32, 34, a pair of lateral incisors 36, 38, a pair of cuspids 40, 42 and terminates at a pair of first bicuspids 44, 46. If treatment of second the bicuspids 48, 50, is desired, the peripheral outline 24 and strip dimensions can be appropriately modified.

Figure 4:
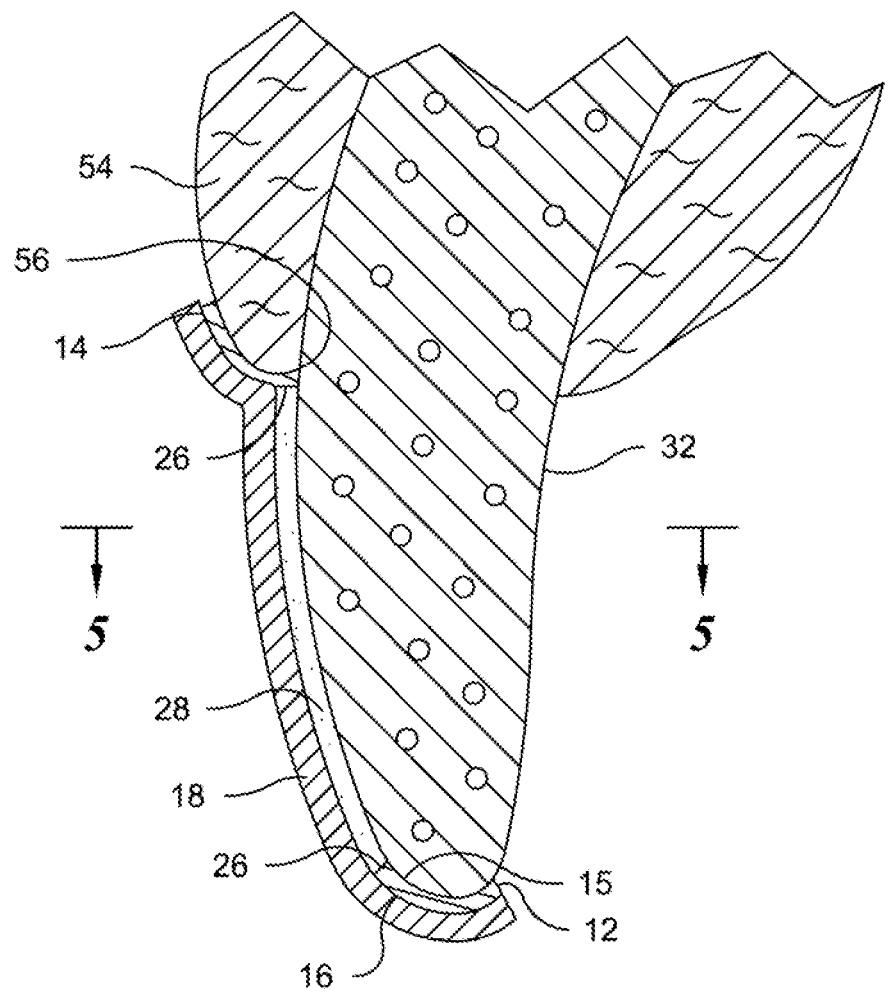
FIG. 4 is an enlarged scale sectional view through a central incisor during administration of the dental preparation.

From an examination of FIG. 4 wherein the central incisor 32 and adjacent gingival tissue 54 are illustrated, it will be observed that the lowermost portion of the sealing strip 12 extends to the edge of the occlusal surface, with the tacky surface of the border 15 sealing against and adhering thereto. Optionally, the strips 12 and 18 may extend below or be bent across the occlusal surfaces. The uppermost portion of the sealing strip 12 extends across gingival tissue 54, however the internal wall 26 is preferably positioned adjacent a gingival border 56, so as to minimize contact between the dental preparation 28 and the gingival tissue 54.

Upon completion of the prescribed treatment duration the delivery system is removed and discarded.

Thus it will be seen that there is provided dental preparation delivery system which achieves the various aspects, features and considerations of the present invention and which is well adapted to meet the conditions of practical usage.

Since various possible embodiments might be made of the present invention and since various changes might be made in the exemplary embodiments set forth herein without departing from the spirit of the invention, is to be understood that all matter herein described or shown in the accompanying drawings is to be interpreted as illustrative and not in a limiting sense.

Having thus described the invention, there is claimed as new and desired to be secured by Letters Patent:

1. A dental preparation delivery system comprising a sealing strip formed of a soft malleable wax and a base strip, the base strip having a higher elastic modulus than the sealing strip, the strips being adhered to one another, a receptacle extending into the thickness of the sealing strip, the receptacle comprising a peripheral outline of a dentition, the peripheral outline being defined by a continuous internal wall within the sealing strip, the peripheral outline being surrounded by a border, wherein
   i) the receptacle is filled with a dental preparation;
   ii) when said sealing strip is overlaid with a removable film it forms a chamber encasing said dental preparation; and
   iii) the dental preparation can be administered to buccal surfaces of a user's dentition by registration of the peripheral outline with the buccal surfaces and urging the base strip against the buccal surfaces to reshape the sealing strip border to the contours of the user's dentition.

2. A dental preparation delivery system of claim 1 wherein the sealing strip is formed of dental wax.

3. A dental preparation delivery system of claim 2 wherein the base strip is formed of wax.

4. A dental preparation delivery system of claim 1 wherein the peripheral outline is in the shape of a model dentition.

5. A dental preparation delivery system of claim 1 wherein the internal wall extends completely through the thickness of the sealing strip, a portion of the base strip being in registration with the peripheral outline, the internal wall and the portion of the base strip in registration with the peripheral outline forming the receptacle.

6. A dental preparation delivery system of claim 1 wherein the delivery system is bent into an arch shape for administration of the dental preparation.

7. A dental preparation delivery system of claim 1 wherein the dental preparation is selected from the group consisting of a bleaching agent, a desensitizing agent, an anticariogenic agent, an antimicrobial agent and a fluoride.

8. A dental preparation delivery system of claim 1 wherein the internal wall extends partially through the thickness of the sealing strip, leaving a portion of the sealing strip as a floor surrounded by the internal wall, the internal wall and the floor forming the receptacle.

9. A dental preparation delivery system of claim 1 wherein a portion of the border adheres to the user's gingival tissue during administration of the dental preparation.

10. A dental preparation delivery system of claim 1 wherein a portion of the border adheres to tooth surfaces adjacent occlusal surfaces of the user's dentition during administration of the dental preparation.

11. A dental preparation delivery system comprising a laminate formed of a the sealing strip and a base strip, sealing strip being soft and malleable, the base strip having a higher elastic modulus than the sealing strip, the strips being adhered to one another, a receptacle extending into the thickness of the sealing strip, the receptacle including a peripheral outline in the shape of a model dentition, the peripheral outline being defined by a continuous internal wall within the sealing strip, the sealing strip including a border extending between the peripheral outline and the outer periphery of the sealing strip, a dental preparation filled within the receptacle, the delivery system further comprising a removable film overlay covering the dental preparation and the border and which forms a chamber encasing said dental preparation.

12. A dental preparation delivery system of claim 11 wherein the sealing strip is formed of wax and the base strip is formed of wax.

13. A dental preparation delivery system of claim 11 wherein the internal wall extends partially through the thickness of the sealing strip, leaving a portion of the sealing strip as a floor surrounded by the internal wall, the internal wall and the floor forming the receptacle.

14. A dental preparation delivery system of claim 11 wherein the dental preparation is selected from the group consisting of a bleaching agent, a desensitizing agent, an anticariogenic agent, an antimicrobial agent and a fluoride.

15. A dental preparation delivery system of claim 11 wherein the internal wall extends completely through the thickness of the sealing strip, a portion of the base strip being in registration with the peripheral outline, the internal wall and the portion of the base strip in registration with the peripheral outline forming the receptacle.

16. A dental preparation delivery system of claim 11 wherein the dental preparation comprises a bleaching agent.

17. A method of delivering a dental preparation with the dental preparation delivery system of claim 11, the method comprising the steps of:
   a) removing the film overlay,
   b) bending the delivery system to an arch shape to approximate the curvature of a user's dentition arch,
   c) registering the peripheral outline with the corresponding surfaces of the user's buccal dentition, and
   d) contacting and sealing surfaces of the user's buccal dentition with the dental preparation by applying lateral pressure in a lingual direction against the base strip to deform and shape the sealing strip until the border conforms to the shape of and adheres to the peripheral outline of the user's buccal dentition.

18. A method of delivering a dental preparation in accordance with claim 17, the method including the further step of:
   e) maintaining the delivery system in position for a prescribed treatment duration.

19. A method of delivering a dental preparation in accordance with claim 18, the method including the further step of:
   f) removing the delivery system after the prescribed treatment duration has expired.

20. A dental preparation delivery system of claim 12 wherein the sealing strip is formed of boxing wax and the base strip is formed of modelling wax or base plate wax.

21. A dental preparation delivery system of claim 3 wherein the sealing strip is formed of boxing wax and the base strip is formed of modelling wax or base plate wax.

22. A dental preparation delivery system of claim 1 wherein the base strip is formed of modelling wax or base plate wax.

* * * * *